United States Patent
Rüegg

[11] Patent Number: 6,063,732
[45] Date of Patent: May 16, 2000

[54] HERBICIDAL SYNERGISTIC COMPOSITION AND METHOD OF WEED CONTROL

[75] Inventor: Willy T. Rüegg, Gipf-Oberfrick, Switzerland

[73] Assignee: Novartis Crop Protection, Inc., Greensboro, N.C.

[21] Appl. No.: 09/142,298

[22] PCT Filed: Mar. 3, 1997

[86] PCT No.: PCT/EP97/01055
§ 371 Date: Sep. 3, 1998
§ 102(e) Date: Sep. 3, 1998

[87] PCT Pub. No.: WO97/34485
PCT Pub. Date: Sep. 25, 1997

[30] Foreign Application Priority Data

Mar. 15, 1996 [CH] Switzerland ............... 692/96

[51] Int. Cl.$^7$ ............ A01N 37/22; A01N 43/10; A01N 43/80
[52] U.S. Cl. ............................................. 504/140
[58] Field of Search ............................................. 504/140

[56] References Cited

U.S. PATENT DOCUMENTS

| | | | |
|---|---|---|---|
| 5,002,606 | 3/1991 | Moser et al. | 71/118 |
| 5,457,085 | 10/1995 | Seckinger et al. | 504/289 |
| 5,556,828 | 9/1996 | Glock et al. | 504/105 |

FOREIGN PATENT DOCUMENTS

| | | |
|---|---|---|
| 2 150 781 | 12/1995 | Canada . |
| 0 616 770 | 9/1982 | European Pat. Off. . |
| 0 614 606 | 9/1994 | European Pat. Off. . |
| 0 685 157 | 12/1995 | European Pat. Off. . |
| 96/03877 | 2/1996 | WIPO . |

OTHER PUBLICATIONS

Research Disclosure, No. 372, Elmsworth, GB, pp. 271 and 271,XP000509081, "Neue Herbizide Mittle" (in German), (1995).
Luscombe, B.M. et al., Brighton Crop Protection Conference—Weeds, vol. 1, pp. 35–42 (1995).
The Pesticide Manual, 10th Ed. pp. 345–346.
Chemical Abstracts, vol. 97, No. 9, abstract No. 71671, dated Aug. 30, 1982.
Worthing, C.R. (Editor), The Pesticide Manual, 9th Edition, p. 61, 1991.

*Primary Examiner*—S. Mark Clardy
*Attorney, Agent, or Firm*—Michael P. Morris; William A. Teoli, Jr.; Irving M. Fishman

[57] ABSTRACT

The invention relates to compositions comprising: (a) a 4-benzoylisoxazole of formula (I), wherein R, $R^1$, $R^2$ and n are as defined in the description and (b) a chloroacetamide herbicide; and their use as herbicides.

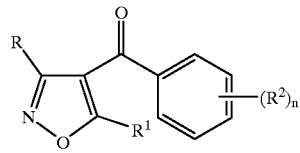

(I)

9 Claims, No Drawings

HERBICIDAL SYNERGISTIC COMPOSITION AND METHOD OF WEED CONTROL

The present invention relates to a novel herbicidal synergistic composition that comprises a combination of herbicides suitable for selectively controlling weeds in crops of cultivated plants, typically in crops of cereals, maize, rice, rape, sugar beer, sugar cane, plantations, cotton and soybeans.

The invention further relates to a process for controlling weeds in crops of cultivated plants and to the use of said novel composition therefor.

The compounds of formula I

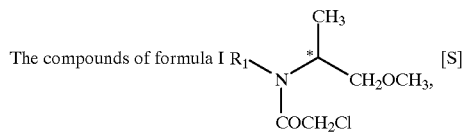
(I)

wherein $R_1$ is the

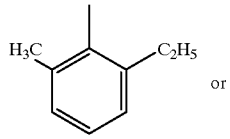
($A_1$)

or

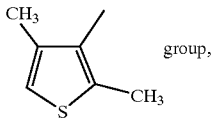
($A_2$)

group, have herbicidal activity, as is disclosed, inter alia, in U.S. Pat. No. 5,002,606 and U.S. Pat. No. 5,457,085.

The following compound of formula II

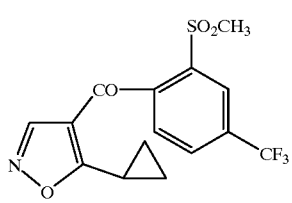
(II)

is also known as herbicide, inter alia from BRIGHTON CROP PROTECTION CONFERENCE—Weeds—1995, Proceedings Volume 1, pages 35–42. Synergistic mixtures of compounds of formula II with the racemates of formula I are disclosed in WO 96/03877.

Surprisingly, it has now been found that a variable amount of a combination of two active ingredients, i.e. of an active ingredient of formula I with an active ingredient of formula II exerts a synergistic effect that is able to control the majority of weeds preferably occurring in crops of cultivated plants preemergence as well as postemergence, without substantial injury to the cultivated plants.

Accordingly, this invention proposes a novel synergistic composition for selectively controlling weeds, which comprises, in addition to conventional inert formulation assistants, as active ingredient on the one hand a compound of formula I

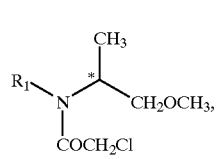
(I)

wherein $R_1$ is the

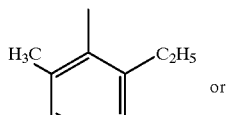
($A_1$)

or

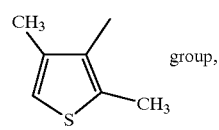
($A_2$)

group, and, on the other hand, a synergistically effective amount of the active ingredient of formula II

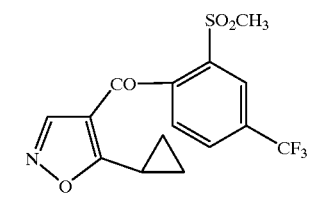
(II)

in admixture with each other.

The compounds of formula I are the optical isomers aRS,1'S(−)-N-(1'-methyl-2'-methoxyethyl)-N-chloroacetyl-2-ethyl-6-methylaniline and (1S,aRS)-2-chloro-N-(2,4-dimethyl-3-thienyl)-N-(2-methoxy-1-methylethyl) acetamide.

It is highly surprising that the combination of an active ingredient of formula I with an active ingredient of formula II has a greater additive action against the weeds to be controlled than to be expected in principle and thus enhances the activity range of both active ingredients in particular in two respects:

On the one hand, the rates of application of the single compounds I and II are reduced while the effectiveness of said compounds is retained. On the other hand, the novel combination also achieves a high degree of weed control where the single compounds have become no longer agriculturally effective at low rates of application. The consequence is a substantial broadening of the activity spectrum against weeds and an additional increase in the selectivity for the cultivated plants that is necessary and desirable in the event of unintentional overapplication of herbicide. Furthermore, the novel composition permits more flexibility in subsequent crops while retaining the excellent control of weeds in cultivated plants.

The novel herbicidal compositions can be used against a great number of agriculturally important weeds, including Stellaria, Agrostis, Digitaria, Avena, Setaria, Sinapis, Lolium, Solanum, Echinochloa, Scirpus, Monochoria, Sagittaria, Bromus, Alopecurus, Sorghum halepense, Rottboellia, Cyperus, Abutilon, Sida, Xanthium, Amaranthus, Chenopodium, Ipomoea, Chrysanthemum, Galium, Viola and Veronica.

The novel compositions are suitable for all standard methods of application used in agriculture, typically preemergence application, postemergence application and seed dressing.

The novel herbicidal combination is preferably suitable for weed control in crops of cultivated plants, typically cereals, rape, sugar beet, sugar cane, plantains, rice, maize and soybeans as well as for non-selective weed control. The novel combination is preferably used in maize and soybeans.

Crops will be understood as meaning also those crops that have been made tolerant to herbicides or classes of herbicides by conventional breeding or genetic engineering methods.

The novel herbicidal combination contains the active ingredient of formula I and the active ingredient of formula II in any ratio, but usually with an excess of the one component over the other. Preferred ratios of the active ingredient of formula II and the component of formula I are in the range from 1:100 to 100:1, prefererably from 1:10 to 10:1.

Very particularly effective synergistic herbicidal compositions have been found to be combinations of the compound of formula I, wherein $R_1$ is the $A_1$ group, with the compound of formula II.

In addition to the compounds of formulae I and II, the novel compositions can contain a safener, in particular Benoxacor. Benoxacor is known, inter alia, from The Pesticide Manual, 9th ed., The British Crop Protection Council, page 61. Benoxacor is known as safener for protecting cultivated plants against the herbicidal action of the compounds of formula I, in particular against that compound of formula I, wherein $R_1$ is the $A_1$ group.

If the novel composition contains a safener, the weight ratio of herbicide of formula I (in particular that of compound of formula I, wherein $R_1$ is the $A_1$ group) to safener is preferably from 5:1 to 40:1, in particular from 20 to 1.

Different methods and techniques may suitably be used for applying safeners or compositions containing them for protecting cultivated plants from the harmful effects of herbicides of formula I, conveniently the following:

i) Seed dressing a) Dressing the seeds with a wettable powder formulation of the safener by shaking in a vessel until the safener is uniformly distributed on the surface of the seeds (dry treatment), using up to c. 1 to 500 g of the active ingredient of formula II (4 g to 2 kg of wettable powder) per 100 kg of seeds.

b) Dressing seeds with an emulsifiable concentrate of the safener by method a) (wet treatment).

c) Dressing by immersing the seeds in a mixture containing 100–1000 ppm of the safener for 1 to 72 hours, leaving them wet or subsequently drying them (seed soaking).

Seed dressing or treatment of the germinated seedlings are naturally the preferred methods of application, as the safener treatment is fully concentrated on the target crop. Usually 1 to 1000 g, preferably 5 to 250 g, of antidote is used per 100 kg of seeds. However, depending on the method employed, which also permits the use of other active ingredients or micronutrients, plus or minus deviations from the indicated limiting concentrations are possible (repeat dressing).

ii) Application as tank mixture

A liquid formulation of a mixture of antidote and herbicide (reciprocal ratio from 10:1 to 1:100) is used, the concentration of herbicide being from 0.05 to 4.0 kg/ha. Such tank mixtures are applied before or after sowing.

iii) Application in the furrow

The safener formulated as emulsifiable concentrate, wettable powder or granulate is applied to the open furrow in which the seeds have been sown. After covering the furrow, the herbicide is applied pre-emergence in conventional manner.

iv) Controlled release of safener

A solution of the safener is applied to mineral granulate substrates or polymerised granulates (urea/formaldehyde) and dried. A coating may additionally be applied (coated granulates) which permits controlled release of the safener over a specific period of time.

The rate of application can vary over a wide range and will depend on the nature of the soil, the type of application (pre- or postemergence, seed dressing, application to the seed furrow; no tillage application etc.), the cultivated plant, the weed to be controlled, the respective prevailing climatic conditions; and on other factors governered by the type of application and the target crop. The herbicidal combination can usually be applied in a rate of application of 0.05 to 4 kg, preferably of 0.5 to 4 kg/ha.

The combinations of the compound of formula I with the compound of formula II may be used in unmodified form, i.e. as obtained in the synthesis, but preferably they are processed in conventional manner with the assistants customarily employed in formulation technology, typically solvents, solid carriers or surfactants, e.g. to emulsifiable concentrates, directly sprayable or dilutable solutions, wettable powders, soluble powders, dusts, granulates or microcapsules. As with the type of compositions, the methods of application such as spraying, atomising, dusting, wetting, scattering or pouring, are chosen in accordance with the intended objectives and the prevailing circumstances.

The formulations, i.e. the compositions containing the active ingredients of formulae I and II and optionally one or more than one formulation assistants, are prepared in per se known manner, e.g. by homogeneously mixing and/or grinding the active ingredient with said formulation assistants, typically solvents or solid carriers. Surface-active compounds (surfactants) may additionally be used for preparing the formulations.

Suitable solvents may typically be: aromatic hydrocarbons, preferably the fractions containing 8 to 12 carbon atoms such as mixtures of xylene or substituted naphthalenes; phthalates such as dibutyl phthalate or dioctyl phthalate; aliphatic hydrocarbons such as cyclohexane or paraffins; alcohols and glycols and their ethers and esters such as ethanol, ethylene glycol, 2-methoxyethanol or 2-ethoxyethanol; ketones such as cyclohexanone, strongly polar solvents such as N-methyl-2-pyrrolidone, dimethylsulfoxide or N,N-dimethylformamide, as well as vegetable oils or epoxidised vegetable oils such as epoxidised coconut oil or soybean oil; or water.

The solid carriers typically used for dusts and dispersible powders are usually natural mineral fillers such as calcite, talcum, kaolin, montmorillonite or attapulgite. To improve the physical properties it is also possible to add highly dispersed silicic acid or highly dispersed absorbent polymers. Suitable granulated adsorptive carriers are porous types, including pumice, broken brick, sepiolite or bentonite; and suitable nonsorbent carriers are materials such as calcite or sand. In addition, innumerable pregranulated materials of inorganic or organic origin may be used, especially dolomite or pulverised plant residue.

Depending on the type of active ingredient of formula I to be formulated, suitable surface-active compounds are nonionic, cationic and/or anionic surfactants or mixtures of surfactants having good emulsifying, dispersing and wetting properties.

Suitable anionic surfactants may be water-soluble soaps as well as water-soluble synthetic surface-active compounds.

Suitable soaps are the alkali metal salts, alkaline earth metal salts, ammonium salts or substituted ammonium salts of higher fatty acids ($C_{10}$–$C_{22}$), e.g. the sodium or potassium salts of oleic or stearic acid, or of natural fatty acid mixtures which can be obtained, inter alia, from coconut oil or tallow oil. Further suitable soaps are also the fatty acid methyl taurin salts.

More often, however, so-called synthetic surfactants are used, especially fatty sulfonates, fatty sulfates, sulfonated benzimidazole derivatives or alkylarylsulfonates.

The fatty alcohol sulfonates or sulfates are usually in the form of alkali metal salts, alkaline earth metal salts, ammonium salts or substituted ammonium salts, and they contain a $C_8$–$C_{22}$alkyl radical which also includes the alkyl moiety of acyl radicals, e.g. the sodium or calcium salt of ligninsulfonic acid, of dodecylsulfate, or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain two sulfonic acid groups and one fatty acid radical containing 8 to 22 carbon atoms. Illustrative examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Corresponding phosphates, typically salts of the phosphoric acid ester of p-nonylphenol-(4-14)ethylene oxide, or phospholipids, are also suitable.

Nonionic surfactants are preferably polyglycol ether derivatives of aliphatic or cycloaliphatic alcohols or of saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable nonionic surfactants are the water-soluble polyadducts of poylethylene oxide with polypropylene glycol, ethylenediaminopolypropylene glycol and alkylpolypropylene glycol containing 1 to 10 carbon atoms in the alkyl chain, which polyadduccts contain 20 to 250 ethylene glycol ether groups and 10 to 100 propylene glycol ether groups. These compounds usually contain 1 to 5 ethylene glycol units per propylene glycol unit.

Illustrative examples of nonionic surfactants are nonylphenol polyethoxylates, polyethoxylated castor oil, polyadducts of polypropylene and polyethylene oxide, tributylphenol polyethoxylate, polyethylene glycol and octylphenol polyethoxylate.

Fatty acid esters of polyoxyethylene sorbitan are also suitable nonionic surfactants, typically polyoxyethylene sorbitan trioleate.

Cationic surfactants are preferably quaternary ammonium salts carrying, as N-substituent, at least one $C_8$–$C_{22}$ alkyl radical and, as further substituents, unsubstituted or halogenated lower alkyl, benzyl or hydroxy-lower alkyl radicals. The salts are preferably in the form of halides, methyl sulfates or ethyl sulfates, for example stearyl trimethylammonium chloride or benzyl bis(2-chloroethyl) ethylammonium bromide.

The surfactants customarily employed in the art of formulation are described, inter alia, in "Mc Cutcheon's Detergents and Emulsifiers Annual" MC Publishing Corp., Ridgewood, N.J., 1981, Stache, H., "Tensid-Taschenbuch", Carl Hanser Verlag, München/Wien, 1981 and M. and J. Ash, "Encyclopedia of Surfactants", Vol I–III, Chemical Publishing Co., New York, 1980–81.

The herbicidal formulations usually contain from 0.1 to 99% by weight, preferably from 0.1 to 95% by weight, of active ingredient mixture of the compound of formula I with the compound of formula II, from 1 to 99.9% by weight of a solid or liquid formulation assistant, and from 0 to 25% by weight, preferably from 0.1 to 25% by weight, of a surfactant.

Whereas it is preferred to formulate commercial products as concentrates, the end user will normally use dilute formulations.

The compositions may also contain further ingredients such as stabilisers, vegetable oils or epoxidised vegetable oils (epoxidised coconut oil, rape seed oil or soybean oil), antifoams, e.g. silicone oil, preservatives, viscosity regulators, binders, tackifiers, as well as fertilisers or other active ingredients.

Preferred formulations are those composed of:
(%=percent by weight)
Emulsifiable concentrates compound mixture: 1 to 90%, preferably 5 to 20% surfactant: 1 to 30%, preferably 10 to 20% liquid carrier: 5 to 94%, preferably 70 to 85%

Dusts compound mixture: 0.1 to 10%, preferably 0.1 to 5% solid carrier: 99.9 to 90%, preferably 99.9 to 99%

Suspension concentrates compound mixture: 5 to 75%, preferably 10 to 50% water: 94 to 24%, preferably 88 to 30% surfactant: 1 to 40%, preferably 2 to 30%

Wettable powders compound mixture: 0.5 to 90%, preferably 1 to 80% surfactant: 0.5 to 20%, preferably 1 to 15% solid carrier: 5 to 95%, preferably 15 to 90%

Granulates compound mixture: 0.1 to 30%, preferably 0.1 to 15% solid carrier: 99.5 to 70%, preferably 97 to 85%

The invention is illustrated by the following non-limitative Examples.

Formulation Examples for mixtures of herbicides of formulae I and II (%=percent by weight)

| F1. Emulsifiable concentrates | a) | b) | c) | d) |
|---|---|---|---|---|
| compound mixture | 5% | 10% | 25% | 50% |
| calcium dodecylbenzenesulfonate | 6% | 8% | 6% | 8% |
| polyethoxylated castor oil (36 mol EO) | 4% | — | 4% | 4% |
| octylphenol polyethoxylate (7–8 mol EO) | — | 4% | — | 2% |
| cyclohexanone | — | — | 10% | 20% |
| mixture of aromatic hydrocarbons $C_9$–$C_{12}$ | 85% | 78% | 55% | 16% |

Emulsions of any desired concentration can be prepared by diluting such concentrates with water.

| F2. Solutions | a) | b) | c) | d) |
|---|---|---|---|---|
| compound mixture | 5% | 10% | 50% | 90% |
| 1-methoxy-3-(3-methoxy- | — | 20% | 20% | — |

| F2. Solutions | a) | b) | c) | d) |
|---|---|---|---|---|
| propoxy)propane polyethylene glycol MG 400 | 20% | 10% | — | — |
| N-methyl-2-pyrrolidone | — | — | 30% | 10% |
| mixture of aromatic hydrocarbons $C_9$–$C_{12}$ | 75% | 60% | — | — |

The solutions are suitable for use as microdrops.

| F3. Wettable powders | a) | b) | c) | d) |
|---|---|---|---|---|
| compound mixture | 5% | 25% | 50% | 80% |
| sodium ligninsulfonate | 4% | — | 3% | — |
| sodium laurylsulfate | 2% | 3% | — | 4% |
| sodium diisobutylnaphthalene-sulfonate | — | 6% | 5% | 6% |
| octylphenol polyethoxylate (7–8 mol EO) | — | 1% | 2% | — |
| highly dispersed silicic acid | 1% | 3% | 5% | 10% |
| kaolin | 88% | 62% | 35% | — |

The compound is thoroughly mixed with the adjuvants and this mixture is ground well in a suitable mill to give wettable powders which can be diluted with water to give suspensions of any desired concentration.

| F4. Coated granulates | a) | b) | c) |
|---|---|---|---|
| compound mixture | 0.1% | 5% | 15% |
| highly dispersed silicic acid | 0.9% | 2% | 2% |
| inorganic carrier (Æ 0.1–1 mm) e.g. $CaCO_3$ or $SiO_2$ | 99.0% | 93% | 83% |

The compound is dissolved in methylene chloride, the solution is sprayed on to the carrier, and the solvent is removed under vacuum.

| F5. Coated granulates | a) | b) | c) |
|---|---|---|---|
| compound mixture | 0.1% | 5% | 15% |
| polyethylene glycol MG 200 | 1.0% | 2% | 3% |
| highly dispersed silicic acid | 0.9% | 1% | 2% |
| inorganic carrier (Æ 0.1–1 mm) e.g. $CaCO_3$ or $SiO_2$ | 98.0% | 92% | 80% |

The finely ground compound is uniformly applied in a mixer to the carrier moistened with polyethylene glycol. Non-dusty coated granulates are obtained in this manner.

| F6. Extruder granulates | a) | b) | c) | d) |
|---|---|---|---|---|
| compound mixture | 0.1% | 3% | 5% | 15% |
| sodium ligninsulfonate | 1.5% | 2% | 3% | 4% |
| carboxymethyl cellulose | 1.4% | 2% | 2% | 2% |
| kaolin | 97.0% | 93% | 90% | 79% |

The compound is mixed with the adjuvants and the mixture is moistened with water. This mixture is extruded and then dried in a stream of air.

| F7. Dusts | a) | b) | c) |
|---|---|---|---|
| compound mixture | 0.1% | 1% | 5% |
| talcum | 39.9% | 49% | 35% |
| kaolin | 60.0% | 50% | 60% |

Ready for use dusts are obtained by mixing the compound with the carriers on a suitable mill.

| F8. Suspension concentrates | a) | b) | c) | d) |
|---|---|---|---|---|
| compound mixture | 3% | 10% | 25% | 50% |
| ethylene glycol | 5% | 5% | 5% | 5% |
| nonylphenol polyethoxylate (15 mol EO) | — | 1% | 2% | — |
| sodium ligninsulfonate | 3% | 3% | 4% | 5% |
| carboxymethyl cellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 87% | 79% | 62% | 38% |

The finely ground compound is intimately mixed with the adjuvants to give a suspension concentrate from which suspensions of any desired concentration can be prepared by dilution with water.

It is often more expedient to formulate the active ingredient of formula I and the component of formula II individually and only to combine them shortly before application in the applicator in the desired mixture ratio as tank mixture in water.

BIOLOGICAL EXAMPLES

Example H1: The following test compares the action of a composition of this invention, comprising as active ingredients the enantiomer aRS,1'S(−)-N-(1'-methyl-2'-methoxyethyl)-N-chloroacetyl-2-ethyl-6-methylaniline of formula Ia

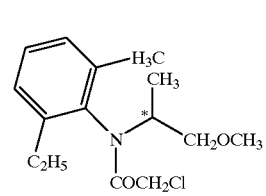

(Ia)

and the compound of formula II

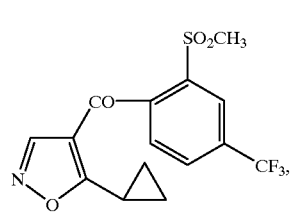

(II)

DISCLOSURE, April 1995/271, No. 37242, comprising the racemic compound N-(1'-methyl-2'-methoxyethyl)-N-chloroacetyl-2-ethyl-6-methylaniline of formula A

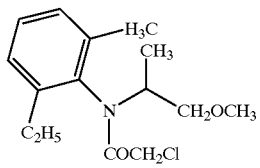

(A)

and the cited compound of formula II.

Pre-emergence application in maize

Monocot and dicot weeds and cultivated plants (maize P3737) are sown in plastic pots in standard soil. Immediately after sowing, the test substances are applied in aqueous suspension (500 l water/ha). The rates of application for the compound of formula Ia or its racemate are 1000, 500 and 250 g/ha, and the rate of application for the compound of formula II is 120 g/ha. The test plants are then raised in a greenhouse under optimum conditions. Evaluation is made after 4 weeks (% action, 100%=plant withered, 0%=no phytotoxic action). The results are shown in the following Table B1.

What is claimed is:

1. A herbicidal synergistic composition, comprising one or more inert formulation assistants, a synergistically effective combined amount of a compound of formula I

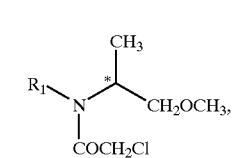

(I)

wherein $R_1$ is the

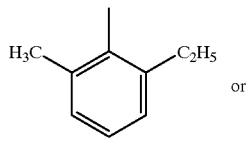

(A₁)

or

TABLE B1

Herbicidal action in crops of maize:

| Plant | Novel composition ||| Composition of the prior art |||
|---|---|---|---|---|---|---|
| | 1000 g/ha Ia + 120 g/ha II | 500 g/ha Ia + 120 g/ha II | 250 g/ha Ia + 120 g/ha II | 1000 g/ha A + 120 g/ha II | 500 g/ha A + 120 g/ha II | 250 g/ha A + 120 g/ha II |
| Maize | 10 | 5 | 0 | 20 | 10 | 5 |
| abutilon theophrasti | 100 | 100 | 100 | 100 | 100 | 100 |
| amaranthus retroflexus | 100 | 100 | 100 | 100 | 100 | 100 |
| euphorbia heterophylla | 100 | 98 | 98 | 95 | 95 | 95 |
| panicum miliaceum | 100 | 100 | 100 | 100 | 100 | 100 |
| setaria faberi | 100 | 100 | 100 | 100 | 100 | 100 |
| sorghum bicolor | 100 | 100 | 100 | 100 | 100 | 100 |
| xanthium canadense | 95 | 95 | 90 | 90 | 90 | 90 |

Table B1 shows that the composition of this invention has advantages with respect to the herbicidal action in the weeds Euphorbia heterophylla and *Xanthium canadense*. This is taken to be the result of the enhanced herbicidal activity of the enantiomer of formula Ia over the racemate of formula A. Surprisingly, however, it is found that despite this enhanced activity the damage that the novel composition causes on maize is reduced by 50% as compared to the known composition. At a rate of application of 250 g/ha of formula Ia there is even no damage at all to be observed on the cultivated plants, whereas the composition of the prior art at this rate of application damages the cultivated plant already to 5%. The enhanced protection of the maize by the novel composition is of extremely great agricultural importance and is completely unexpected given the content of the more active enantiomer compared to the known racemate. A valuable practical consequence thereof is that the unintentional overapplication of the novel composition in maize is substantially less critical than in the case of the racemic composition.

Comparable results are obtained for the mixture of the compound of formula I, wherein A is A₂, with the compound of formula II.

-continued

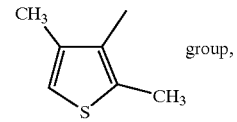

(A₂)

group, and a compound of formula II

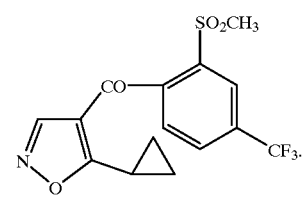

(II)

2. A herbicidal composition according to claim 1, comprising a compound of formula I, wherein $R_1$ is the $A_1$ group.

3. A herbicidal composition according to claim 1, wherein the weight ratio of the compound of formula I to the compound of formula II is from 1:100 to 100:1.

4. A method of controlling undesirable plant growth in crops of cultivated plants, which comprises treating the cultivated plant, plant part, seed or the locus thereof with a herbicidally effective amount of a composition as claimed in claim 1.

5. A method according to claim 4, wherein the cultivated plants, plant parts or seeds are cereals, rape, sugar beet, sugar cane, plantains, rice, maize or soybeans.

6. A method according to claim 4, which comprises treating crops of cultivated plants with said composition at rates of application corresponding to 0.05 to 4 kg of said synergistically effective combined amount of said compounds of formula I and formula II per hectacre.

7. A composition according to claim 1, comprising, in addition to the compounds of formulae I and II, benoxacor.

8. A method according to claim 4, which comprises treating the cultivated plant, plant part, seed or the locus thereof at separate times with the compound of formula I and with the compound of formula II.

9. A method according to claim 4, which comprises treating the cultivated plant, plant part, seed or the locus thereof at separate times with the compound of formula I together with benoxacor and with the compound of formula II.

* * * * *